(12) United States Patent
Wagoner et al.

(10) Patent No.: US 7,064,309 B2
(45) Date of Patent: Jun. 20, 2006

(54) METHOD FOR DETECTING FOREIGN OBJECT DEBRIS

(75) Inventors: Daniel E. Wagoner, Florissant, MO (US); Michael L. Taylor, Collinsville, IL (US); John C. Clayton, Genevieve, MO (US); John D. Fitts, St. Charles, MO (US); Greg L. Benfer, St. Charles, MO (US); Lynn E. Johnson, Warrenton, MO (US)

(73) Assignee: The Boeing Company, Chicago, IL (US)

( * ) Notice: Subject to any disclaimer, the term of this patent is extended or adjusted under 35 U.S.C. 154(b) by 867 days.

(21) Appl. No.: 09/954,404

(22) Filed: Sep. 17, 2001

(65) Prior Publication Data

US 2003/0052286 A1    Mar. 20, 2003

(51) Int. Cl.
 *G01C 21/00* (2006.01)
(52) U.S. Cl. ................ 250/203.1; 250/458.1; 250/302
(58) Field of Classification Search ............ 250/203.1, 250/203.2, 221, 222.2, 458.1, 459.1, 492.1, 250/573–577, 356.02, 356.01, 559.29, 559.32, 250/559.44, 559.4, 302; 422/82.05, 82.07–82.08
See application file for complete search history.

(56) References Cited

U.S. PATENT DOCUMENTS

| | | | |
|---|---|---|---|
| 1,664,397 A | 4/1928 | Bens | |
| 3,534,589 A | 10/1970 | Gibbons et al. | |
| 3,758,215 A | 9/1973 | Paruolo et al. | |
| 3,911,733 A | 10/1975 | Bhuta et al. | |
| 3,988,530 A | 10/1976 | Ikegami et al. | |
| 4,787,990 A | 11/1988 | Boyd | |
| 4,792,276 A | 12/1988 | Krawiec et al. | |
| 4,798,386 A | 1/1989 | Berard | |
| 5,311,639 A | 5/1994 | Boshier | |
| 5,370,387 A | 12/1994 | Baker | |
| 5,453,356 A | 9/1995 | Bard et al. | |
| 5,569,766 A | 10/1996 | Waggoner et al. | |
| 5,575,074 A | 11/1996 | Cottongim et al. | |
| 5,876,995 A | 3/1999 | Bryan | |
| 5,959,306 A | 9/1999 | Kalley et al. | |
| 6,150,656 A * | 11/2000 | Garrity | 250/302 |
| 6,210,973 B1 | 4/2001 | Pettit | |
| 6,268,222 B1 | 7/2001 | Chandler et al. | |

* cited by examiner

*Primary Examiner*—Thanh X. Luu
*Assistant Examiner*—Stephen Yam
(74) *Attorney, Agent, or Firm*—Ostrager Chong Flaherty & Broitman P.C.

(57) ABSTRACT

A method for detecting a non-fixed object in a system (12) is provided. The method includes applying a light emitting substance (13) to at least a portion (14) of an object (10). At least a section (20) of the portion (14) is illuminated with a non-fixed object illuminator (16). The object (10) is detected in the system (12) in response to illuminating the section (20). The object (10) is then determined to be a fixed or non-fixed object.

24 Claims, 1 Drawing Sheet

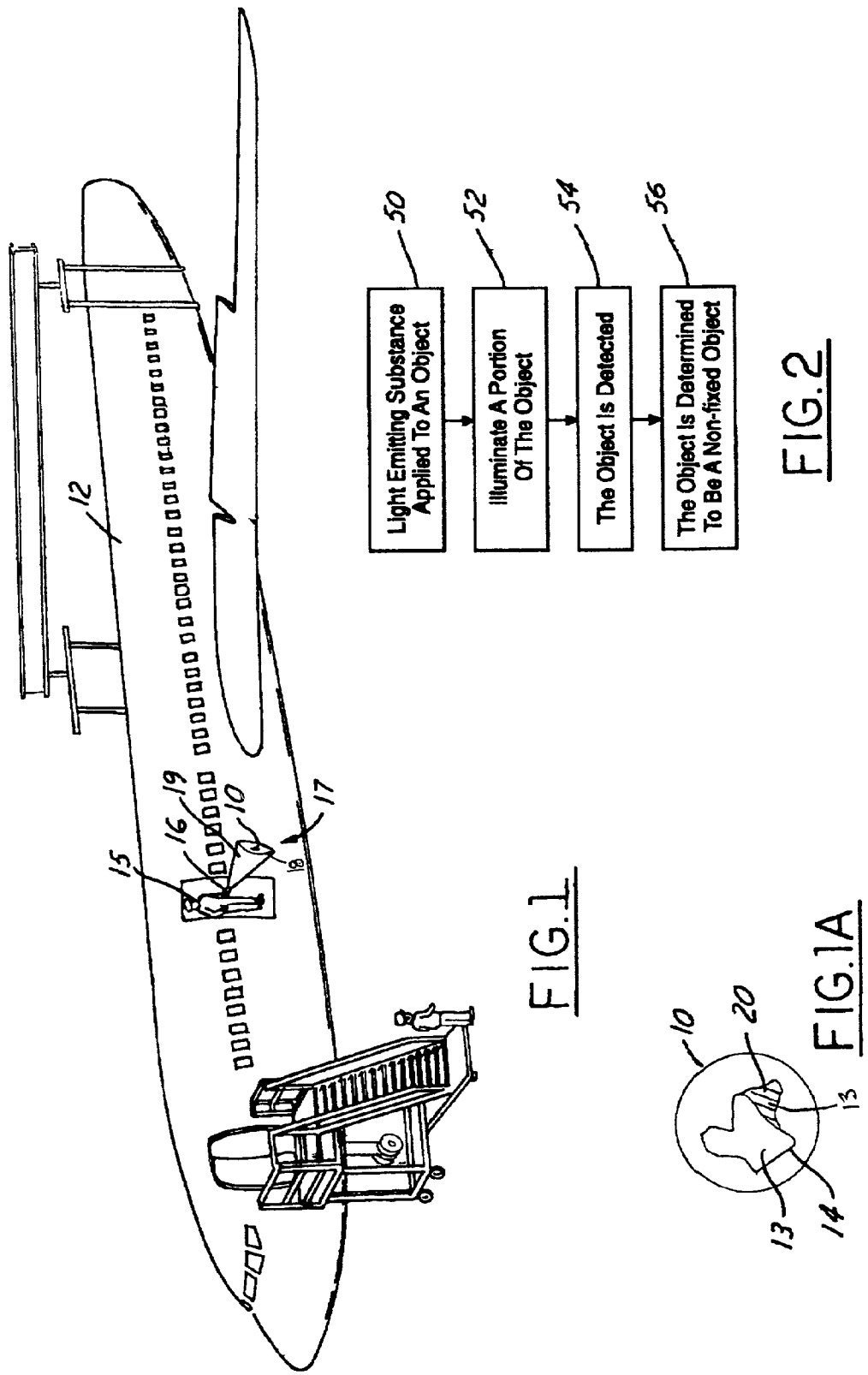

METHOD FOR DETECTING FOREIGN OBJECT DEBRIS

TECHNICAL FIELD

The present invention relates generally to object detection methods, and more particularly to a method for detecting foreign object debris on an aircraft.

BACKGROUND OF THE INVENTION

Aircraft safety is an ongoing concern for aircraft producers. An unknown loose object on board an aircraft may cause an aircraft to malfunction or not operate as designed thereby decreasing safety of the aircraft. Unknown loose objects are referred to as foreign object debris (FOD) in the art. FOD are difficult to detect and many hours of searching an aircraft for FOD occur during production of an aircraft, to assure the aircraft is free from loose objects, before the aircraft leaves a production facility or is operated. Moreover, because the detection of FOD relies almost solely on visual inspection, it can be subject to human error.

FOD are of various size and shape and can go undetected in large aircraft. A large aircraft has various cavities, pockets, and crevices that cause the process of detecting FOD to be difficult. For example, a small FOD item, such as a rivet or nut, lying in a dark crevice may go undetected during the search of a large aircraft. The larger the amount of undetected FOD the increased likelihood of an aircraft system malfunctioning.

It would therefore be desirable to develop an improved efficient technique for detecting FOD that reduces the time and costs involved in manufacturing of an aircraft.

SUMMARY OF THE INVENTION

The foregoing and other advantages are provided by a method of detecting a non-fixed object in a system. The method includes applying a light emitting substance to at least a portion of an object. At least a section of the portion is illuminated with a non-fixed object illuminator. The object is detected in the system in response to illuminating the section. The object is then determined to be a fixed or non-fixed object.

One of several advantages of the present invention is that it provides an improved method for detecting non-fixed objects within an aircraft.

Another advantage of the present invention is that it provides an efficient method for detecting non-fixed objects within an aircraft.

In accordance with the above and other advantages of the present invention, production costs of an aircraft are reduced. Costs are reduced directly due to decreased time and energy in searching for non-fixed objects. Costs are also reduced indirectly as a result of potential decreases in post manufacturing costs due to aircraft malfunction caused by non-fixed objects going undetected.

The present invention itself, together with attendant advantages, will be best understood by reference to the following detailed description, taken in conjunction with the accompanying figures.

BRIEF DESCRIPTION OF THE DRAWING

For a more complete understanding of this invention reference should now be had to the embodiments illustrated in greater detail in the accompanying figures and described below by way of examples of the invention wherein:

FIG. 1 is a representative illustration of implementing a method of detecting a non-fixed object in an aircraft in accordance with a preferred embodiment of the present invention;

FIG. 1A is a representative illustration of an object having a light emitting substance and detected on the aircraft in accordance with a preferred embodiment of the present invention; and FIG. 2 is a flow chart illustrating the method of FIG. 1 in accordance with a preferred embodiment of the present invention.

DETAILED DESCRIPTION OF THE PREFERRED EMBODIMENT

While the present invention is described with respect to a method for detecting non-fixed objects within an aircraft, the present invention may be adapted to be used for a variety of other components and systems including automotive vehicles, electronic or mechanical systems, machinery, or other components or systems that may require detection of a non-fixed object. The present invention may also be used in various production and manufacturing processes including before, during, and after assembly of a system. In the following description, various operating parameters and components are described for one constructed embodiment. These specific parameters and components are included as examples and are not meant to be limiting.

Referring now to FIG. 1, a representative illustration of implementing a method of detecting a non-fixed object 10 in an aircraft 12 in accordance with an embodiment of the present invention is shown. The object 10 may be any of the following objects which may be non-fixed objects: a tool, a system object, a non-system object, a loose or free moving object, a shaving, a chip, a free moving object, or other non-fixed object. A non-fixed object refers to an object that is loose or not fixed to the aircraft.

Referring now also to FIG. 1A, representative illustration of the object 10 having a light emitting substance 13 and detected on the aircraft 12 in accordance with a preferred embodiment of the present invention is shown. The object 10 has the light-emitting substance 13 applied to at least a portion 14 thereof, which is capable of being detected, by an operator 15, using a non-fixed object illuminator 16. For example, with respect to the aircraft 12, the light-emitting substance 13 may be applied to at least a portion of any object that is not intended to be fixed to the aircraft 12 or an object that may have a high probability of becoming loose or unfixed from the aircraft 12. Once an object has been subjected to the light-emitting substance 13, it can be detected by the non-fixed object illuminator 16. In accordance, with the preferred system, the operator 15 walks around the aircraft 12 with the non-fixed object illuminator 16 to look for objects that are not fixed to the aircraft 12. The object 10 is in a location 17 on the aircraft 12. The non-fixed object illuminator 16 is operated in order to illuminate an area 18 of location 17. The illumination of the area 18 is represented by beam 19, in a close proximity to the object 10 so as to illuminate at least a section 20 of the portion 14. When the object 10 is illuminated it may be determined to be a non-fixed object, in which case the object 10 may be fastened to the aircraft 12 or removed from the aircraft 12.

Referring now to FIG. 2, a flow chart illustrating a method of detecting a non-fixed object in an aircraft in accordance with an embodiment of the present invention is shown. In accordance with the preferred method, the light emitting substance 13 is applied to at least a portion of the object 10, as generally indicated by reference number 50. The object 10 may be a system object or a non-system object. Exemplary system objects include panstock items such as rivets, bolts, nuts, platenuts, Hi-loks, cotter pins, or other panstock items. Exemplary system objects may also include objects that are to be attached or fixed to the aircraft. A non-system object may be a tool, a shaving, a chip, or other object that is not to be attached or fixed to the aircraft.

The light emitting substance 13 may consist of any of the following: a coating, a paint, a dye, a stain, a powder, a tape, a fabric, a sheet or other light emitting substance, which is known in the art. The light emitting substance 13 may also be produced from a material that is fluorescent, phosphorescent, luminescent, incandescent, photoluminescent, hotoluminescent, or other material that emits light. An example of a fluorescent dye that may be used is a fluorescent dye from ITW Dymon-Dykem product number DYX-163. The light emitting substance 13 may be applied to the object 10 using any of the following processes: painting, dipping, spraying, marking, taping, coating, or other process known in the art. An example of a reflective tape that may be used is a tape from 3M Scotchcal™, which is identified by product number 7,725,404-7,725,414.

For example as to differentiate between objects, fluorescent dye may be applied to panstock so as to detect and signify to the operator 15 that the detected non-fixed object is a panstock item. Additionally, tools used to manufacture the aircraft may have reflective tape applied to them as to differentiate detected tools from panstock. Tools include pliers, screwdrivers, wrenches, air tools, and any other tools that are used in the production of an aircraft. The operator 15 may therefore upon detection of a non-fixed object more effectively determine, in response to the type of reflection that is associated with a type of object, what appropriate action is required.

In accordance with the method, at least a portion of the object 10 is illuminated with the non-fixed object illuminator 16, as generally indicated by reference number 52. The non-fixed object illuminator 16 may be any of the following: an ultraviolet light (black light), a fluorescent light, or a white light. The non-fixed object illuminator 16 may be operated manually by the operator 15 or through the use of an automated machine. The non-fixed object illuminator 16 is powered as to illuminate areas throughout the aircraft 12 as to detect any non-fixed objects.

The object 10 is detected in the aircraft 12 in response to illuminating the portion 14, as generally indicated by reference number 54. The detected object may be any object having the light emitting substance 13 applied to it. The operator may then determine as described in the following step 56 that the object is fixed or not fixed to the aircraft 12.

Therefore, the object 10 is determined to be a non-fixed object as generally indicated by reference number 56. The operator 15 then performs the appropriate action to either remove the detected non-fixed object, fasten the non-fixed object to the aircraft 12, or determine that no action need be performed on the object.

The above described method may also be used after performing a production task such as drilling a hole, tightening an object, attaching an object, removing an object, or other production task. For example, when drilling a hole, the light emitting substance 13 may be a lubricant having a fluorescent powder, which may be applied to a drill-bit or a surface being drilled such that the light emitting substance 13 sticks to or attaches to any shavings or chips that are created during drilling of the hole. The non-fixed object illuminator 16 may then be used to detect the shavings or chips, such that the operator 15 may remove of them as desired.

The present invention provides an efficient and improved technique for detecting non-fixed objects within an aircraft. The technique is quick, easy, and inexpensive to perform. The technique saves costs involved in production and manufacturing of an aircraft and post manufacturing costs caused by component malfunctions due to undetected non-fixed object.

The above-described apparatus, to one skilled in the art, is capable of being adapted for various purposes and is not limited to the following systems: automotive vehicles, electronic or mechanical systems, machinery, or other components or systems that may require detection of a non-fixed object. The above-described invention may also be varied without deviating from the spirit and scope of the invention as contemplated by the following claims.

What is claimed is:

1. A method of detecting a non-fixed fastener within an aircraft that requires fastening or removal therefrom, comprising:
    applying a light emitting substance to at least a portion of the non-fixed fastener;
    illuminating at least a section of said portion with a non-fixed object illuminator;
    detecting the non-fixed fastener in the aircraft in response to illuminating said section; and
    determining whether to remove the non-fixed fastener from the aircraft or whether to fasten the non-fixed fastener to the aircraft.

2. The method of claim 1 further comprising:
    determining said detected non-fixed fastener to be of a certain type of object.

3. The method of claim 3 further comprising:
    determining whether to perform an action to said detected non-fixed fastener in response to determining said type of said detected non-fixed fastener.

4. The method of claim 1 wherein applying a light emitting substance to at least a portion of the non-fixed fastener comprises applying a light emitting substance to at least a portion of the non-fixed fastener from at least one of a system object and a non-system object.

5. The method of claim 1 wherein applying a light emitting substance comprises a process from at least one of painting, dipping, marking, taping, and coating.

6. The method of claim 1 wherein illuminating at least a section of said portion with a non-fixed object illuminator comprises illuminating at least a section of said portion with a non-fixed object illuminator from at least one of a ultraviolet light, a fluorescent light, and a white light.

7. The method of claim 1 wherein illuminating at least a section of the non-fixed fastener is performed manually by an operator or by an automated machine.

8. The method of claim 1 wherein applying a light emitting substance comprises applying a light emitting substance from at least one of a light emitting: coating, a paint, a dye, a stain, a powder, a tape, a fabric, and a sheet.

9. The method of claim 1 wherein applying a light emitting substance comprises applying a light emitting substance from at least one of a fluorescent substance, a phosphorescent substance, a luminescent substance, an incandescent substance, and a photoluminescent substance.

10. The method of claim 1 wherein applying a light emitting substance to at least a portion of the non-fixed fastener comprises attaching a reflective material to at least a portion of said non-fixed fastener.

11. A method of detecting a non-fixed object in a system during production or manufacturing of the system comprising:
   applying a light emitting substance to at a portion of an object;
   performing a production or manufacturing task;
   illuminating at least a section of said portion with a non-fixed object illuminator;
   detecting said object in the system in reponse to illuminating said section; and
   determining said object to be a non-fixed object.

12. The method of claim 11 wherin performing a production or manufacturing task comprises at least one of the following: drilling a hole, attaching an object, removing an object, and fastening an object.

13. The method of claim 11 further comprising: determining whether to remove said detected non-fixed object from the system, whether to fasten said non-fixed object.

14. The method of claim 11 further comprising: determining said detected object to be of a certain type of object.

15. The method of claim 14 further comprising: determining whether to perform an action to said detected object in reponse to determining said type of said detected object.

16. A method of detecting a non-fixed object in a system comprising:
   applying a light emitting substance to at least a portion of each object in a plurality of objects;
   illuminating at least a section of each of said portions with a non-fixed object illuminator;
   detecting said plurality of objects in the system in response to illuminating said sections;
   determining said objects to be non-fixed objects.

17. A method of detecting foreign object debris within an aircraft that requires removal therefrom so as to prevent malfunctioning of the aircraft, comprising:
   applying a light emitting substance of at least a portion of a non-fixed object;
   illuminating at least a section of said portion with a non-fixed object illuminator;
   detecting said non-fixed object in the aircraft in response to illuminating said section;
   determining said non-fixed object to be foreign object debris; and
   removing the non-fixed object from the aircraft.

18. The method of claim 17 further comprising:
   determining whether to remove said detected non-fixed object from the system, whether to fasten said non-fixed object to the system, or whether to perform any action at all to said detected non-fixed object.

19. The method of claim 17 further comprising:
   determining said detected non-fixed object to be of a certain type of object.

20. The method of claim 19 further comprising:
   determining whether to perform an action to said detected non-fixed object in response to determining said type of said detected non-fixed object.

21. The method of claim 17 wherein detecting said non-fixed object comprises detecting a non-fixed object from at least one of a tool, a system object, a non-system object, a loose object, a shaving, a chip, and a free moving object.

22. The method of claim 17 wherein illuminating at least a section of said non-fixed object is performed manually by an operator or by an automated machine.

23. The method of claim 17 wherein applying a light emitting substance to at least a portion of a non-fixed object comprises applying a light emitting substance to at least a portion of said non-fixed object from at least one of a tool, a panslock item, a shaving, a chip, a surface, an object attached to the system, and an object not attached to the system.

24. The method of claim 17 wherein applying a light emitting substance to at least a portion of a non-fixed object comprises attaching a reflective material to at least a portion of said non-fixed object.

* * * * *